United States Patent [19]

Hope

[11] Patent Number: Plant 5,613

[45] Date of Patent: Dec. 24, 1985

[54] IMPATIENS PLANT NAMED VISTA IMPATIENS NO. 56

[75] Inventor: Claude Hope, Cartago, Costa Rica

[73] Assignee: Pan American Plant Company, Parrish, Fla.

[21] Appl. No.: 566,806

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant, known by the cultivar name Vista Impatiens No. 56, characterized by its large, vivid poppy orange colored flowers with white eyes, profuse flowering, dark green foliage, tall and upright habit, and by its moderate rate of growth and good self-branching habits, making the cultivar ideal for bedding plants and pot culture.

1 Drawing Figure

The present invention relates to a new and distinctive cultivar of impatiens plant, botanically known as *Impatiens,* and referred to by the cultivar name Vista Impatiens No. 56.

The new cultivar is the result of a planned program of hybridization the purpose of which was to obtain a series of plants having a wide range of colors and very large flowers derived from the New Guinea complex of species collected by the Longwood Garden Expedition of 1970. The seedling comprising the new cultivar was selected in 1981 and designated as seedling No. 3428-1. The new cultivar was developed through controlled breeding by crossing seedling No. 3180-1 (from Impatiens Schlecterii P.I. 354260)×seedling No. 3351-1, of unknown origin.

Asexual reproduction by terminal or stem cuttings taken by me at Cartago, Costa Rica has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Vista Impatiens No. 56 was selected primarily for its vivid poppy orange colored flowers, which have a white eye in the center.
2. Flower size is large (58–60 cm.).
3. Plant flowers abundantly in optimum conditions (80° F. nights and 60° F. days).
4. Foliage is dark green in color, providing an excellent contrast with the flower color.
5. Rate of growth is moderate, producing in 6–8 weeks in a 5½" pot a saleable plant 30–40 cm. tall and 35 cm. in diameter when grown under full sun in the fall, winter and spring months and under light shade in the summer in Florida.
6. Habit is tall (45–60 cm. when full grown) and upright, making it suitable for bedding plants, pot and larger container culture.
7. Exhibits good self-branching.

The accompanying colored photograph illustrates the overall appearance of this cultivar, showing the colors as true as it is reasonably possible to obtain in a colored reproduction of this type.

The following is a detailed description of my new impatiens cultivar based on plants produced under commercial practice in Cortez and Parrish, Fla. The plants were grown outdoors in full sun during the fall, winter and spring months and under light shade during the summer months. Color references are made to The Royal Horticultural Society Colour Chart except where general terms of ordinary dictionary significance are used.

Parentage: Seedling No. 3180-1 (from Impatiens Schlecterii P.I. 354260)×3351-1, a seedling of unknown origin.

Propagation:

A. *Type cutting.*—Tip cutting with 5 cm. stems.

B. *Time to initiate roots.*—10–14 (Days) at 27° C. summer; 12–16 (days) at 18° C. winter.

C. *Rooting habit.*—Abundant and fibrous.

Plant description:

A. *Form.*—Tall and upright (45–60 cm. tall); good self-branching.

B. *Habit of growth.*—Rate of growth moderate for this type of plant. Vegetative shoots are formed at the lower nodes and flowers at the higher nodes.

C. *Foliage description.*—Lower leaves opposite, higher leaves in whorls of 5. Leaves are simple. (1) Size: Average full grown leaf is 115 mm. long×40 mm. wide. Full grown leaves have petioles 10 mm. long. Young leaves have little to no petioles. (2) Shape: Elliptic, apex cuminate, base attenuate. (3) Texture: Smooth surface, glabrous. (4) Margin: Serrulate. (5) Color: Young foliage, top side close to 137C, under side between 138A and B; mature foliage, top side 137A, under side between 138A and B. (6) Venation: Pinnate, main vein becomes infused with red as leaf matures.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with three sepals. Upper two sepals are 11 mm. long×5 mm. wide, apex acuminate. Lower sepal is 15 mm. long×10 mm. wide, apex acuminate.

Upper sepals green, lower sepal colorless infused with pink (base upward) and green (apex downward); apex green. A hollow spur (25 mm. long when full grown) is connected to base of lower sepal and is colorless but heavily infused with pink.

D. *Flowers borne.*—On peduncles 55 mm. long, green in color.

E. *Quantity of flowers.*—One flower per leaf, occurring progressively around the whorl of leaves.

F. *Petals.*—(1) Shape: Top petal heart-shaped with a rounded base, other petals heart-shaped with pointed bases. Occasionally a lobe will be noted where the petal curves to form top of heart shape. (2) Color: top side when opening between but much brighter than orange-red 33A-B. Each flower has a pink to white large eye in the center. The main portion of the petal fades to between red 40A and B; under side, close to red 40C. (3) Number of petals: Five; the middle and bottom petals are slightly united at the base on each side. (4) Size of flowers: Top petal is 28 mm. long×31 mm. wide; 2 lower petals are 31 mm. long×25 mm. wide. Total flower diameter is 58 mm.

G. *Reproductive organs.*—(1) Stamens: Five; with the lower stamen being shorter than the others. Stamens united in an asymmetrical tube surrounding and covering the ovary. (a) anthers: hooded, colorless, infused with red-orange. (b) pollen color: cream. (2) Pistils: (a) Stigma: Five-pointed star, colorless. (b) Styles: Cream, very short. (c) Ovaries: Five, celled, size 5 mm., green in color.

Disease resistance:

No general plant diseases noted. Insect problems can include the two-spotted spider mite which can cause foliar injury and thrips which can cause stunting and injury to the growing tip.

I claim:

1. A new and distinct cultivar of impatiens plant, known by the cultivar name Vista Impatiens No. 56, as described and illustrated, and characterized by its large, vivid poppy orange colored flowers with white eyes, profuse flowering, dark green foliage, tall and upright habit, and by its moderate rate of growth and good self-branching habits, making the cultivar ideal for bedding plants and pot culture.

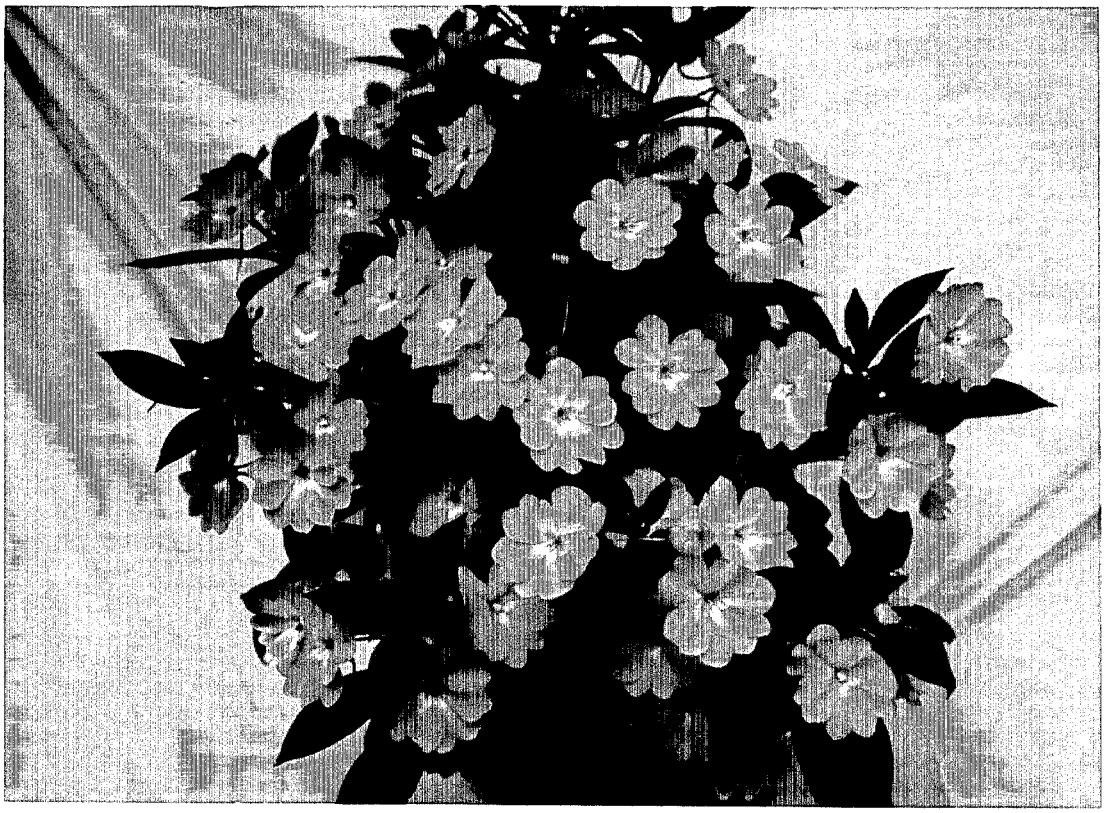

* * * * *